United States Patent
Pendleton et al.

(10) Patent No.: US 11,083,635 B2
(45) Date of Patent: Aug. 10, 2021

(54) TAMPON DELIVERY SYSTEM FOR A PHARMACEUTICAL, HOLISTIC OR MEDICINAL COMPONENT

(71) Applicant: Herphoric, LLC, Fairfield, OH (US)

(72) Inventors: Nicholas Patrick Pendleton, Trenton, OH (US); Albert Michael Fischer, Fairfield, OH (US); James Kinney, Cincinnati, OH (US)

(73) Assignee: Herphoric, LLC, Fairfield, OH (US)

( * ) Notice: Subject to any disclaimer, the term of this patent is extended or adjusted under 35 U.S.C. 154(b) by 0 days.

(21) Appl. No.: 17/139,137

(22) Filed: Dec. 31, 2020

(65) Prior Publication Data

US 2021/0205149 A1    Jul. 8, 2021

Related U.S. Application Data

(60) Provisional application No. 62/956,811, filed on Jan. 3, 2020.

(51) Int. Cl.
*A61F 13/20*    (2006.01)
*A61K 31/05*    (2006.01)
(Continued)

(52) U.S. Cl.
CPC ...... *A61F 13/2074* (2013.01); *A61F 13/2068* (2013.01); *A61F 13/2071* (2013.01); *A61F 13/2085* (2013.01); *A61F 13/266* (2013.01); *A61K 9/0036* (2013.01); *A61K 31/05* (2013.01); *D06C 27/00* (2013.01); *A61F 2013/15097* (2013.01); *D10B 2509/026* (2013.01)

(58) Field of Classification Search
CPC ............ A61F 13/15211; A61F 13/2074; A61F 13/2068; A61F 13/2071; A61F 13/2085; A61F 13/266; A61F 2013/15097; A61K 9/4808; A61K 9/0036; A61K 31/05; D10B 2509/026

USPC ...... 604/364, 359, 360, 385.17, 385.18, 904
See application file for complete search history.

(56) References Cited

U.S. PATENT DOCUMENTS 4,317,447 A * 3/1982 Williams ................. A61J 3/08
                                                          424/433
4,318,405 A    3/1982 Sneider
                    (Continued)

OTHER PUBLICATIONS

Karki et al.; "Thin films as an emerging platform for drug delivery"; Asian Journal of Pharmaceutical Sciences; vol. 11; Oct. 2016; p. 559-574.

(Continued)

*Primary Examiner* — Jacqueline F Stephens
(74) *Attorney, Agent, or Firm* — BakerHostetler

(57) ABSTRACT

A tampon and delivery system for a pharmaceutical, holistic or medicinal component, includes: (1) a tampon having a generally cylindrical shape including a leading end and a cylindrical outer surface; (2) an outer delivery sheath applied to at least a portion of the cylindrical outer surface of the tampon, distal from the leading end (and preferably leaving the leading end exposed), where the outer delivery sheath comprises a formulation including (a) a water soluble polymer film carrier and (b) a pharmaceutical, holistic or medicinal component; and (3) an applicator containing the tampon and applied delivery sheath. Methods for preparation of the delivery system and methods of use are also disclosed.

25 Claims, 2 Drawing Sheets

(51) Int. Cl.
*A61F 13/26* (2006.01)
*D06C 27/00* (2006.01)
*A61K 9/00* (2006.01)
*A61F 13/15* (2006.01)

(56) References Cited

U.S. PATENT DOCUMENTS

| | | | |
|---|---|---|---|
| 6,315,763 B1* | 11/2001 | Albright | A61F 13/2051 604/385.18 |
| 6,359,191 B1* | 3/2002 | Rusch | A61F 13/206 604/364 |
| 6,899,700 B2 | 5/2005 | Gehling et al. | |
| 2005/0256482 A1* | 11/2005 | Minoguchi | A61F 13/2085 604/385.17 |
| 2007/0027096 A1* | 2/2007 | Chen | C12N 15/115 514/44 R |
| 2019/0282513 A1* | 9/2019 | Yerike | A61K 36/185 |
| 2020/0163807 A1 | 5/2020 | Tumey | |
| 2020/0323699 A1 | 10/2020 | Buss | |

OTHER PUBLICATIONS

Bala et al.; "Orally dissolving strips: A new approach to oral drug delivery system" Int. J. Pharm Investigation; vol. 3; 2013; p. 67-76.

\* cited by examiner

TAMPON DELIVERY SYSTEM FOR A PHARMACEUTICAL, HOLISTIC OR MEDICINAL COMPONENT

CROSS-REFERENCE TO RELATED APPLICATIONS

This application claims priority to U.S. Provisional Application, Ser. No. 62/956,811, filed Jan. 3, 2020; the entire disclosure of which is incorporated by reference.

BACKGROUND

In studies, 80 percent of women suffer from menstrual pain. Fifty percent of women experience a heavy flow that impacts their daily activities. Ten percent of women have monthly debilitating symptoms that limit normal daily routine.

On a global perspective, each woman has an estimated 450 menstrual cycles in their lifetime. Each menstrual cycle uses an average of 23 tampons at an average cost of $12.00 per box. The cost of the menstrual cycle is increased due to the cost of pain relief drugs and to the lost work days due to severe menstrual pain. Worldwide, the total cost could be as much as $7,000.00 or more per year per woman.

Prior art tampon delivery systems for therapeutic agents are known. For example, U.S. Pat. No. 6,899,700 to Gehling discloses dipping a tampon into a formulation containing the therapeutic agent. Such a prior art delivery system can result in significant loss of usable therapeutic agent or limit the absorbent properties of the tampon. Another prior art option is to dip the entire tampon and then allow to dry. This results in the fibers being saturated with an oil (typical CBD based options are hydrophobic) which will limit the ability of the tampon to do its job of absorbing the water based menstrual fluid. Ultimately requiring more absorbent material to meet the absorbency standard for a given tampon category (i.e. regular vs. super). The CBD oil that is impregnated into the fibers beyond the surface layer would not be accessible to be dissolved by the vaginal epithelium. This would result in needing a higher dosage applied to the product than is being delivered. Another prior art option is to coat a surface of the tampon material with a formulation prior to forming the tampon material into the cylindrical shape. However, this is then rolled up and compressed to create the tampon shape. This does indeed yield a tampon with therapeutic agent on the entire outside surface, it leaves a high proportion of the coated "outside layer" in successive internal rolled layers. In the case of a W-fold tampon this is similar except the tampon is folded into a W shape instead of rolled and yields a similar result.

SUMMARY

Present disclosure provides a modification of a tried-and-true medical device evolving the device into a delivery solution that offers localized relief for women suffering from menstrual pain, endometriosis and other ailments. The delivery mechanism enables core absorption properties of the tampon while delivering supplements; the delivery mechanism protects the tampon from absorbing the supplements; and the delivery mechanism provides a solubility rate that matches supplement absorption into the bloodstream. The applicator and tampon, in dimensions and materials, follow standard market guidelines.

According to aspects of the current disclosure, a tampon and delivery system for a pharmaceutical, holistic or medicinal component, includes: (1) a tampon having a generally cylindrical shape including a leading end and a cylindrical outer surface; (2) an outer delivery sheath applied to at least a portion of the cylindrical outer surface of the tampon, distal from the leading end (and preferably leaving the leading end exposed), where the outer delivery sheath comprises a formulation including (a) a water soluble polymer film carrier and (b) a pharmaceutical, holistic or medicinal component; and (3) an applicator containing the tampon and applied delivery sheath. Methods for preparation of the delivery system and methods of use are also disclosed.

In a more detailed embodiment, the pharmaceutical, holistic or medicinal component includes CBD. In a further detailed embodiment, the CBD component is up to 50% of the outer delivery sheath.

Alternately, or in addition, the outer delivery sheath is designed so as to not restrict the tampon from radially swelling due to absorbing fluid. Alternately, or in addition, the outer delivery sheath is formulated so as to adhere to vaginal wall. Alternately, or in addition, the outer delivery sheath is about 5 to 6 mm distal from the leading end. Alternately, or in addition, the outer delivery sheath includes about 1 to 100 mg of the pharmaceutical, holistic or medicinal component. Alternately, or in addition, the delivery sheath is about 1 mil to 4 mil in thickness.

Based upon this approach, the pharmaceutical, holistic or medicinal component is released in the right place at the right time. The pharmaceutical, holistic or medicinal component does not pass through the digestive system. The woman does not have to change her habits to deliver the product. The vaginal canal has the highest concentration of receptors. By delivering the medication directly to the receptors, the device effectively delivers pain relief and stress relief. In an embodiment, CBD is used as the pharmaceutical, holistic or medicinal component. CBD can be used to help cramping by applying CBD directly to the affected area effectively delivering pain relief and stress relief. CBD is a nutraceutical in some countries without the same regulatory controls and much faster path to market.

DETAILED DESCRIPTION

Figure 1:
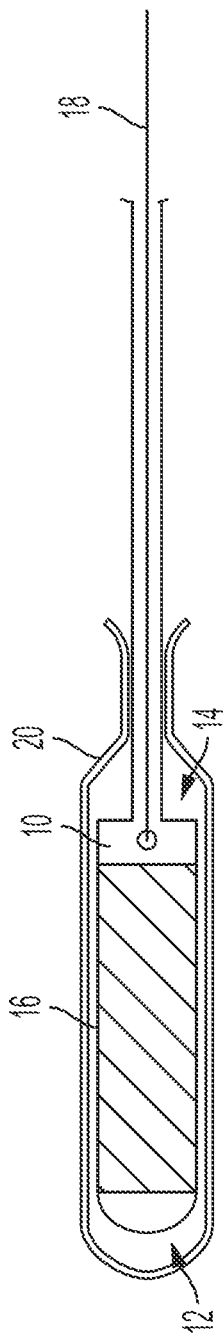
FIG. 1 is a side view of a pharmaceutical, holistic or medicinal delivery mechanism according to an embodiment of the current disclosure, provided on a tampon and positioned in an applicator component where the applicator component is shown in cross-section.
Figure 2:
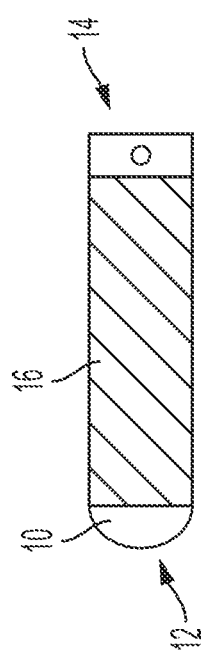
FIG. 2 is a side view of an exemplary pharmaceutical, holistic or medicinal delivery mechanism provided on a tampon, without the applicator component and the removal component.
Figure 3:
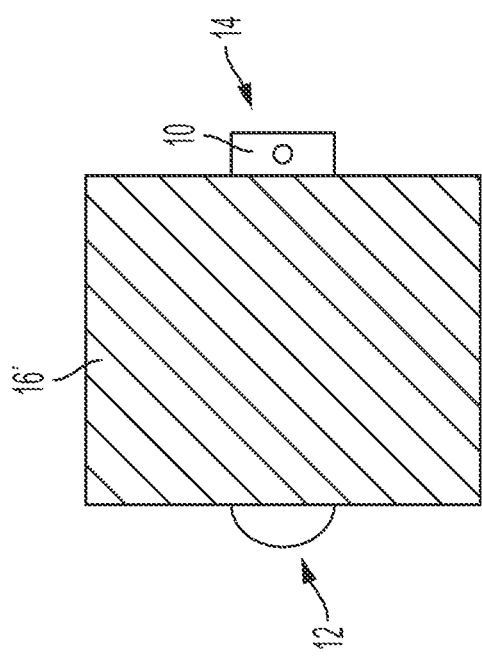
FIG. 3 is a side view of an exemplary pharmaceutical, holistic or medicinal delivery mechanism prior to being installed about a circumference of a tampon.

Referring to FIGS. 1-3, the current disclosure is directed to a tampon and delivery system for a pharmaceutical, holistic or medicinal component (the current disclosure is also directed to methods for constructing such a tampon and delivery system and the current disclosure is also directed to methods for using such a tampon and delivery system). The system includes a conventional tampon 10 having a generally cylindrical shape including a leading end 12, a distal end 14 and a generally cylindrical outer surface. The system also includes an outer delivery layer 16 (or sheath) applied about a portion of the outer cylindrical surface of the tampon, distal from the leading end (i.e., the distal end is substantially free from the outer delivery layer). The outer delivery layer 16 includes a water-soluble polymer film carrier that carries a pharmaceutical, holistic or medicinal component. The tampon may also include a conventional string 18 extending from the distal end and a conventional applicator assembly 20 containing the tampon 10 and outer delivery layer 16.

In an embodiment, the water-soluble polymer film is formulated with the pharmaceutical, holistic or medicinal component before applying to the cylindrical outer surface of the tampon. Such a water-soluble polymer film may be commercially available from a company called ARx, product identification ARCare 93488 non-tacky dissolvable film.

In an embodiment, the pharmaceutical, holistic or medicinal component includes CBD. In a more detailed embodiment, the CBD component may take up to 50 percent of the outer delivery layer. For example, the outer delivery layer may include 100 milligrams of material, where the CBD takes up to 50 milligrams of the delivery layer material.

In a more detailed embodiment, the outer delivery layer 16 is in the form of a sheet (e.g., cut from a web) applied about a portion of the cylindrical outer surface. The outer delivery layer 16 is designed so as not to restrict the tampon from radially swelling upon the tampon absorbing fluid. Further, the outer delivery layer is formulated so as to adhere to the vaginal wall upon expansion within the vaginal canal. In an embodiment, the outer delivery layer 16 is about 5 to about 6 millimeters distal from the leading end 12, which exposes the leading end 12 of the tampon 10 to vaginal fluids upon application. In an embodiment, the outer delivery layer 16 includes about 1 to about 100 milligrams of the pharmaceutical, holistic or medicinal component. In an embodiment, the delivery layer 16 is about 1 mil to about 4 mil in thickness.

In use, when the tampon 10 and delivery layer 16 is inserted into the patient's vaginal canal, the exposed leading end 12 is designed to allow for the absorption of vaginal fluids. Upon absorbing the fluids in the vaginal canal the tampon 10 will swell radially, which will cause the delivery layer 16 to expand outwardly (and breaking apart to allow for the radial swelling) with the radial swelling of the tampon and thus come into greater contact with the patient's vaginal wall. The formulation of the delivery layer 16 allows for the delivery layer to adhere to the patient's vaginal wall which allows for more effective and quick transfer of the pharmaceutical, holistic or medicinal component into the patient's bloodstream. Testing has shown that certain embodiments may be as much as 5× more effective than taking the pharmaceutical, holistic or medicinal component orally. Further, if the pharmaceutical, holistic or medicinal component is CBD, for example, the current device allows the delivery to the bloodstream of the CBD component in the area of menstrual cramps more effectively and quickly.

The formulation of the outer delivery layer is designed to safely dissolve in the patient's body over time. Testing has shown that embodiments of the outer delivery layer 16 effectively and completely dissolve in less than 30 minutes.

An embodiment of the device can be manufactured by first, formulating the water-soluble polymer film with an effective amount of the pharmaceutical, holistic or medicinal component. Then the formulation is cured/hardened in the form of a web of flexible material (sufficiently flexible so that it can be rolled about a tampon and fastened together as a sheath) that is typically between 1 mil to 4 mil in thickness, but may be as thick as up to 20 mil. Next, the web is cut into multiple rectangular tabs 16' as shown in FIG. 3, each of which may be separately wrapped around an outer circumferential surface of a standard tampon 10. Once the tab 16' is wrapped around the outer circumferential surface of the conventional tampon 10, it forms a sheath 16 and is preferably positioned distal from the leading end 12 of the tampon 10, which allows the leading end 12 to substantially immediately start absorbing fluids in the vaginal canal upon application. In an embodiment, the film of the sheath 16 is adhered to itself around the tampon. This can be done via heat, a small amount of moisture and/or by using an adhesive. In an embodiment, the sheath 16 is not directly adhered to the tampon 10, rather the sheath 16 is attached to itself about the tampon 10 tight enough to stay in place on the tampon surface while being inserted. Once inserted, in the presence of vaginal fluids the sheath 16 will separate from the tampon and break apart as the tampon swells. This helps to limit loss of absorption into the tampon.

The above system construction and positioning, and process for installing the sheath 16 about the tampon 10 provides benefits over prior art tampon delivery systems described above. For example, embodiments of the current disclosure do not restrict the ability of the tampon to absorb vaginal fluids as compared to the dipped prior art systems discussed above. Further, because embodiments of the current disclosure do not have the delivery material embedded into the tampon material and because embodiments of the current disclosure are much less likely to experience absorption of the delivery material into the tampon, embodiments of the current disclosure allow for better control of the therapeutic agent doses and properties as compared to the prior art and will allow for less of the formulation/agent to be needed while achieving the same level of systemic absorption of the therapeutic agent.

Once the sheath 16 is applied about the outer circumferential surface of the conventional tampon 10, the tampon and sheath may then be installed into a conventional tampon applicator device 20.

The thickness of the outer delivery layer 16 may be varied during manufacture to control the rate that the delivery layer dissolves; thereby controlling the rate of delivery of the pharmaceutical, holistic or medicinal component to the patient. In one exemplary formulation of the change in thickness exhibited a linear relationship to the dissolution time for an oral test. A 47% reduction in film thickness had on average a 44% reduction in dissolution time. Dissolution time may be also affected by the polymer composition, concentration of the therapeutic, the presence of additives (plasticizers, cellulosics, etc.), moisture uptake in the film and pH.

The disclosed delivery system is effective because it may use conventional tampons and applicators so that the patient will have comfort and practice using the delivery device.

The device provides an axially positioned cylindrical sheath 16 encompassing the tampon's cylindrical outer surface area that can be composed of materials that deliver targeted benefits to the user at a desired solubility rate activated by the vaginal fluids and conditions such as temperature and increasing radial compressive stress as the tampon absorbs fluid from top to bottom thereby causing the tampon to swell both radially and axially. The exposed leading end 12 of the tampon 10 begins immediately absorbing vaginal fluids immediately upon vaginal insertion through the exposed leading end 12 of the device while delaying fluid absorption through the axially positioned cylindrical sheath 16 until the sheath sufficient dissolves from exposure to the vaginal fluids, pH and other conditions. As the tampon 10 takes on fluid and is saturated, it swells thus causing an outward radial force/pressure to exert onto the sheath 16 which can help with the adhesion to the vaginal epithelium. In addition, this saturation and swelling exerts circumferential stress, which helps break up the swelling sheath 16 and allows for more surface area on the vaginal walls for diffusion of the therapeutic agent through the epithelium.

Commercially, tampons are differentiated by their absorbency (e.g., Light, Regular, Super, Super Plus and Super Plus Extra). This is a regulated designation. This is typically accomplished by increasing the amount of absorbent material, which is typically achieved by increasing the circumference of the product, leaving the length substantially unchanged. There are several options for managing size of the sheath 16 for different sized tampons 10. For example, a different formula may be used for each size such that the larger film does not change the dosage. As another example, the film may be sized for the largest product and the amount of overlap would increase on the smaller products. As another example the length of the film could be adjusted to maintain a consistent surface area to control the dosage. In tested prototypes the film length has been in the 35-40 mm range depending on the tampon brand used. While the circumference would be roughly 45-50 mm for a "regular" tampon and 55-60 mm for a "super" tampon.

The current disclosure envisions many possible options for the pharmaceutical, holistic or medicinal component (also referred to herein as the therapeutic agent or the API) in the delivery layer. The current disclosure briefly discusses each of the following groups (pharmaceutical, medical, and holistic) and provides examples of each group that may be included in the polymer film.

The pharmaceuticals group includes a potential list of ingredients. Depending on the application, one pharmaceutical ingredient may be preferred over another (e.g., based on the condition being treated). However, any of the following pharmaceuticals could be added to the polymer solution. The pharmaceuticals may be used appropriately in the polymer solution, independently or in combination, based on FDA approved medical research for the "relief" of or proven "cure" for certain diseases and ailments. The pharmaceuticals group may include one, or a combination of two or more of the following:

1. Antipyretics
2. Analgesics
3. Antimalarials
4. Antibiotics
5. Mood Stabilizers
6. Hormone Replacements
7. Stimulants
8. Tranquilizers
9. Statins
10. Antacids
11. Reflux Suppressants
12. Antiflatulents
13. Antidopaminergics
14. Proton Pump Inhibitors (PPIS)
15. $H_2$-Receptor Antagonists
16. Cytoprotectants
17. Prostaglandin Analogues
18. Laxatives
19. Antispasmodics
20. Antidiarrhoeals
21. Bile Acid Sequestrants
22. Opioids
23. B-Receptor Blockers ("Beta Blockers")
24. Calcium Channel Blockers
25. Diuretics
26. Cardiac Glycosides
27. Antiarrhythmics
28. Nitrates
29. Antianginals
30. Vasoconstrictors
31. Vasodilators
32. ACE Inhibitors
33. Angiotensin Receptor Blockers
34. Beta-Blockers
35. A Blockers
36. Thiazide Diuretics
37. Loop Diuretics
38. Aldosterone Inhibitors
39. Coagulation
40. Anticoagulants
41. Heparin
42. Antiplatelet Drugs
43. Fibrinolytics
44. Anti-Hemophilic Factors
45. Haemostatic Drugs
46. HMG-Coa Reductase Inhibitors
47. Hypolipidaemic Agents
48. Anaesthetics
49. Antipsychotics
50. Antidepressants (Including Tricyclic Antidepressants, Monoamine Oxidase Inhibitors, Lithium Salts, And Selective Serotonin Reuptake Inhibitors (SSRIS))
51. Antiemetics
52. Anticonvulsants/Antiepileptics
53. Anxiolytics
54. Barbiturates
55. Movement Disorder (E.G., Parkinson's Disease) Drugs
56. Stimulants (Including Amphetamines)
57. Benzodiazepines
58. Cyclopyrrolones
59. Dopamine Antagonists
60. Antihistamines
61. Cannabinoids
62. 5-HT (Serotonin) Antagonists
63. Analgesic Drugs
64. Nsaids (Including COX-2 Selective Inhibitors)
65. Muscle Relaxants
66. Neuromuscular Drugs
67. Anticholinesterases
68. Bronchodilators
69. Antitussives
70. Mucolytics
71. Decongestants
72. Corticosteroids
73. Beta2-Adrenergic Agonists
74. Anticholinergics
75. Mast Cell Stabilizers
76. Leukotriene Antagonists
77. Androgens
78. Antiandrogens
79. Estrogens
80. Gonadotropin
81. Corticosteroids
82. Human Growth Hormone
83. Insulin
84. Antidiabetics (Sulfonylureas, Biguanides/Metformin, Thiazolidinediones, Insulin)

85. Thyroid Hormones, A
86. Ntithyroid Drugs
87. Calcitonin
88. Diphosphonate
89. Vasopressin Analogues
90. Alkalinizing Agents
91. Quinolones
92. Cholinergics
93. Antispasmodics
94. 5-Alpha Reductase Inhibitor
95. Selective Alpha-1 Blockers,
96. Sildenafils
97. Fertility Medications
98. Hormonal Contraception
99. Ormeloxifene
100. Haemostatic Drugs
101. Antifibrinolytics
102. Hormone Replacement Therapy (HRT)
103. Bone Regulators
104. Beta-Receptor Agonists
105. Follicle Stimulating Hormone
106. Luteinising Hormone
107. LHRH
108. Gamolenic Acid
109. Gonadotropin Release Inhibitor
110. Progestogen
111. Dopamine Agonists
112. Oestrogen
113. Prostaglandins
114. Gonadorelin
115. Clomiphene
116. Tamoxifen
117. Diethylstilbestrol
118. Antifungals
119. Antileprotics
120. Antituberculous Drugs
121. Antimalarials
122. Anthelmintics
123. Amoebicides
124. Antivirals
125. Antiprotozoals
126. Probiotics
127. Prebiotics
128. Vaccines
129. Immunoglobulins
130. Immunosuppressants
131. Interferons
132. Monoclonal Antibodies
133. Anti-Allergics
134. Antihistamines
135. Corticosteroids
136. Electrolytes
137. Mineral Preparations (Including Iron Preparations And Magnesium Preparations)
138. Parenteral Nutritions
139. Vitamins
140. Anti-Obesity Drugs
141. Anabolic Drugs
142. Haematopoietic Drugs
143. Food Product Drugs
144. Cytotoxic Drugs
145. Therapeutic Antibodies
146. Sex Hormones
147. Aromatase Inhibitors
148. Somatostatin Inhibitors
149. Recombinant Interleukins
150. G-CSF
151. Erythropoietin While there are thousands of different drugs, all marketed drugs fall under one or more tiers of the American Hospital Formulary Service (AHFS) Pharmacologic-Therapeutic Classification System. This classification was developed and is maintained by the American Society of Health-System Pharmacists (ASHP), a national association of pharmacists. The classification includes the following groups of medicines:

1. Antihistamine Drugs (including the prescription drugs Clarinex and Xyzal and OTC medicines Allegra, Benadryl, Claritin, Chlor-Trimeton, Dimetane, Zyrtec and Tavist)
2. Anti-infective Agents (including penicillins and antivirals)
3. Antineoplastic Agents
4. Autonomic Drugs
5. Blood Derivatives
6. Blood Formation, Coagulation, and Thrombosis Agents
7. Cardiovascular Drugs (including digoxin, acebutolol, propranolol and lisinopril)
8. Cellular Therapy
9. Central Nervous System (CNS) Agents (including stimulants and depressants)
10. Contraceptives
11. Dental Agents
12. Diagnostic
13. Electrolytic, Caloric, and Water Balance
14. Enzymes
15. Respiratory Tract Agents
16. Eye, Ear, Nose, and Throat (EENT) Preparations
17. Gastrointestinal Drugs (including rabeprazole sodium, nitazoxanide, bevacizumab and nizatidine)
18. Gold Compounds
19. Heavy Metal Antagonists
20. Hormones and Synthetic Substitutes
21. Local Anesthetics
22. Oxytocics
23. Radioactive Agents
24. Serums, Toxoids, and Vaccines
25. Skin and Mucous Membrane Agents
26. Smooth Muscle Relaxants (including cyclobenzaprine and carisoprodol)
27. Vitamins
28. Miscellaneous Therapeutic Agents
29. Pharmaceutical Aids The holistic group includes a potential list of ingredients, several of which are listed below. The holistic group may include herbal, vitamin, and/or mineral (single or in combination) additives as a remedy for disease and/or pain (mental, physical, or emotional), or discomfort by way of tinctures; essential oils; plant, flower or root extracts; cell salts; sarcodes; nosodes; and vitamins, to name a few. The holistic group may include ingredients used in naturopathic medicine, traditional Chinese and Eastern medicines, and Ayurvedic medicine. This category may also include non-vitamin supplements, such as fish oil, Omega-3 fatty acid, glucosamine, chondroitin, or flaxseed oil. The holistic group may include one or more of the following ingredients:

1. *Ginkgo biloba*
2. *Hypericum perforatum*
3. Herbal pollen extract NOS
4. *Senna alexandrina*
5. Herbal extract NOS
6. *Cimicifuga racemosa*
7. *Echinacea purpurea*
8. *Plantago ovata*

9. *Serenoa repens*
10. *Glycine max*
11. *Oenothera biennis*
12. *Vitis vinifera*
13. *Cannabis sativa*
14. *Cannabis indica*
15. *Mentha* x *piperita*
16. *Citrus* x *paradisi*
17. *Valeriana officinalis*
18. *Silybum marianum*
19. *Viscum album*
20. *Allium sativum*
21. *Vitex agnus-castus*
22. *Pelargonium reniforme* root
23. *Digitalis purpurea*
24. *Ginseng* NOS
25. Humic acid
26. Vitamin A, B-6, B-12, C, D, E, K
27. Chromium
28. Folic acid
29. Calcium
30. Iron
31. Zinc
32. Plant, Fruit and Nut tinctures, concentrates or extracts In one embodiment, the water-soluble polymer film 16 is preferentially formulated using a combination of natural polymers such as pullulan, sodium alginate, maltodextrin, gelatin, or starch. Combining two or more of which can allow the formulator the flexibility to balance between several important properties such as solubility in water, viscosity, mucoadhesion, swelling, film formation, and mechanical properties. These properties can be further enhanced with the use of plasticizers and small quantities of surfactants. However, this should not limit the use of synthetic polymers, such as HPMC, CMC, HPC, PCL, PVA, PVP, or PEO, which one or more, or in combination with the natural polymers offer a range of benefits and could be particularly useful to overcome the compatibility challenges or short comings with various therapeutic agents and their impacts on the film properties.

A representative formula can fall within the following composition ranges on a weight basis, but should not be limiting due to the unique needs of a particular therapeutic agent:

| | |
|---|---|
| Therapeutic Agent(s) | ~5-50% |
| Water Soluble Polymer(s) | ~30-70% |
| Plasticizer(s) | ~0-20% |
| Surfactant(s) | ~0-5% |
| Filler(s) | ~0-5% |

The following Table 1 is a non-exhaustive list of possible polymers for use with exemplary formulations, along with information about each of the polymer's properties and key findings.

TABLE 1

| Polymer | Type | Mw range | H$_2$O Solubility | Mucoadhesion | Swelling | Key Comments |
|---|---|---|---|---|---|---|
| Pullulan | Natural | 8,000-2,000,000 | High | High | Moderate | Can benefit from blending with other polymers |
| Sodium Alginate | Natural | 10,000-600,000 | High | High | High | High compatibility with other polymers |
| Pectin | Natural | 30,000-100,000 | High | High | High | Forms brittle film |
| Gelatin | Natural | 15,000-250,000 | Temperature dependent | Low-Moderate | High | Temperature dependent properties |
| Hydroxypropyl methylcellulose (HPMC) | Synthetic | 10,000-1,500,000 | Moderate | Moderate | Moderate | Can assist in delayed release properties |
| Carboxymethyl cellulose (CMC) | Synthetic | 90.000-700,000 | High | High | High | Good in combination with alginates |
| Poly (vinyl pyrrolidone) (PVP) | Synthetic | 2,500-3,000,000 | Moderate | High | High | Best properties when blended with other polymers |
| Poly (vinyl alcohol) (PVA) | Synthetic | 20,000-200,000 | High | Moderate | High | Forms very flexible film |

This Table 1 is based upon information found the following article: Karki, et. al., *Thin Films as an Emerging Platform for Drug Delivery* (Asian Journal of Pharmaceutical Sciences, June 2016). Another informative article is Bala, et. al., *Orally Dissolving Strips: A New Approach to Oral Drug Delivery System* (Int J Pharm Investig April-June 2013). Each of these articles are incorporated herein by reference.

The type, proportion, and chemical nature of plasticizers may affect the film formation from polymeric aqueous dispersions and as result, the final properties of the film. Indeed, polyols such as polyethylene glycol (PEG), diethylene glycol (DEG), glycerol (GLY), xylitol, sorbitol, fructose, and sucrose are considered as effective plasticizers to improve some properties of biopolymer films.

Surfactants or surface active agents can be used to aid in dispersing, wetting, solubilizing, and emulsifying to enable a more homogenous mixture or solution. This is especially important when using otherwise incompatible ingredients such as the use of a lipophilic therapeutic in a hydrophilic polymer system. The proper selection of which can result in a more stable film and can aid in the dissolution in an aqueous media as well as to aid in the overall absorption of the therapeutic agent. Typical surfactants used can include sodium laurel sulfate, benzalkonium chloride, polyoxymethylene stearates, poloxamers, as well as Tween, and Span type products among others.

Fillers is a more generic category which can include a range of additives in low concentrations. These can include additives for aesthetic purposes such as colorants like TiO2 or be used for rheology modification of the liquid film during manufacturing or as a stabilizing agent in the solid film. This can include a range of cellulosics or natural gums such as xanthan gum, locust bean gum, or carrageenan.

Mucoadhesive properties of the delivery layer 16 may arise from the polymer component as shown above in Table 1.

Figure 4:
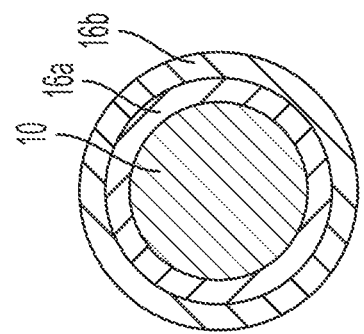
FIG. 4 is a cross-sectional view of an exemplary two-layer delivery mechanism positioned on a tampon.

Certain embodiments of the current disclosure may utilize multiple layers in the composition of the film 16. For example, as shown in FIG. 4, an exemplary film 16 may include a radially inner layer 16a and a radially outer layer 16b, where the radially outer layer 16b that is in initial contact with the mucosa is formulated to dissolve faster than the radially inner layer 16a. Such a radially outer layer 16b may provide a larger dose of the therapeutic for quicker initial relief with a lower dose of the therapeutic in the slower dissolving radially inner layer 16a for a long term relief. As another example, one of the layers 16a, 16b may include a first therapeutic agent while the other layer may include a second therapeutic agent 16a, 16b. The first therapeutic agent may be formulated/selected to have a more local effect while the second therapeutic agent may be formulated/selected to have a more systemic uptake. As another example, the radially inner layer 16a may be formulated as a slower-dissolving protective layer that protects the more quickly dissolving outer layer 16b from being absorbed into the tampon prior to diffusion through the epithelial layers. As another example, the inner layer 16a may be used more as a non-absorbing (or substantially slower absorbing) adhesive or barrier layer that does not include a therapeutic agent. Such a non-absorbing inner layer 16a may allow the outer layer 16b to have a slower dissolution time, which may be an option for a longer release mechanism. As another example, the outer layer 16b may be formulated to give additional mechanical properties to the sheath 16 in the case that the therapeutic agent in the inner layer 16a is difficult to incorporate or requires a formulation that lacks certain properties need for manufacturing or storage/distribution.

Various formulation adjustments can be made between the different layers 16a, 16b to change the dissolution properties. This can be done though polymer selection by utilizing the inherent properties of a chemical structure or by modifying the molecular weight or polydispersity, as an example increasing the molecular weight of a polymer can have positive benefits on mechanical properties, but often leads to a decrease in solubility in part due to an increases in chain entanglement. Alternatively, this can also be adjusted via the use of other additives such as plasticizers or surfactants. Increasing plasticizer content often has a negative impact of solubility, while surfactants can be used to increase the wetting/swelling properties of the polymer which can aid in solubility.

Examples of a localized therapeutic agent could be a probiotic such as a *lactobacillus* species or mixture to balance the vaginal microbiome or an antibiotic such as Metronidazole or Clindamycin for the treatment of bacterial vaginosis. Examples of a therapeutic which can exhibit a systemic mode of action could include analgesics or cannabinoids.

Testing

Referring to FIGS. 2 and 3, initial testing used a 34 mm×40 mm rectangle of the PVOH water-soluble polymer film 16 wrapped about the outer circumferential surface of a testing tampon 10 as showing in FIG. 2 (34 mm axial length and 40 mm circumferential length). The testing sample was tested in a tampon testing device known as a "syngina". A final mist of water spray was sprayed into the inner surface of the simulated vaginal canal before inserting the tampon 10 with the film 16 applied to the tampon, where the sprayed mist was intended to simulate or mimic the mucosal fluid lining the vaginal walls. The testing device then added fluid to the leading end 12 of the tampon to test the device and observe both the tampon function and the dissolving of the film 16 as it absorbed fluids within the simulated vagina. Upon observation, it was seen that the film 16 adhered nicely to the simulated vaginal walls and didn't impede the absorbing functions of the tampon 10. The tampon was able to absorb through the leading end 12 and none of the absorbed fluids leaked out of the tampon. Further, the formulation of the film 16 allowed the film to break apart as the tampon swelled so as to not impede the radial swelling of the tampon.

Testing of this device with human subjects for one hour resulted in an almost complete dissolving of the film 16 prior to removal.

A next test was conducted using a conventional "light" tampon and a 35×35 mm strip of the water-soluble polymer film 16' applied about the outer circumference of the light tampon to form a sheet. The tester made four products using the light tampons. Subjects tested the tampons by using them for one-hour time frames.

A third test was conducted with a strip of 20×37 mm water-soluble polymer film 16' applied about an outer circumferential surface of a regular size conventional tampon 10 that was received within a conventional plunger-style applicator 20 (20 mm axial length×37 mm circumferential length). The testing subjects tested the tampons for one hour at a time. The samples tested well with no problems. Samples were used for one hour by the test subjects, and the film 16 was fully dissolved from the used tampon 10.

Fourth Test. Pharmacokinetic testing of one embodiment of a water-soluble polymer film formulation using Ibuprofen as the therapeutic agent via vaginal administration in a porcine model resulted in an improvement to systemic absorption over a comparable dosing of a traditional orally administered tablet widely used in the market today. In fact the vaginally delivered film reached a matching plasma concentration to the $C_{MAX}$ (peak concentration) of the orally administered Ibuprofen tablet in ~40% of the time, while reaching a ~65% higher $C_{MAX}$ and a higher relative bioavailability over the same 4 hour time window. This illustrates that an efficacious dose can be achieved with the administration of a much lower dose via the use of this invention vs. traditional means. It also does not take into the account the speed of local tissue absorption vs. an alternative route of administration which would further differentiate the benefits of this embodiment of the invention. These tests were conducted using a formulation containing Ibuprofen at ~50% concentration of an ~11 mil thick, 40 mm×50 mm solid film, comprised primarily of a combination of natural polymers as mentioned above with a sugar alcohol based plasticizer and a nonionic surfactant.

Having described the inventions by the above disclosure and the attached drawing, it will be apparent that modifications may be made to the various embodiments disclosed without departing from the scope of the invention as claimed in the appended claims.

What is claimed is:

1. A tampon and delivery system for a pharmaceutical, holistic or medicinal component, comprising:
   a tampon having a generally cylindrical shape including a leading end and a cylindrical outer surface;
   an outer delivery layer applied to at least a portion of the cylindrical outer surface of the tampon, the outer delivery layer positioned at a distance from the leading end of the tampon so as to expose the leading end of the tampon, the outer delivery layer including (a) a water soluble polymer film carrier formulated with (b) a pharmaceutical, holistic or medicinal component; and
   an applicator containing the tampon and the applied outer delivery layer.

2. The tampon and delivery system of claim 1, wherein the pharmaceutical, holistic or medicinal component includes CBD.

3. The tampon and delivery system of claim 2, wherein the CBD component is up to 50% of the outer delivery layer.

4. The tampon and delivery system of claim 1, wherein the outer delivery layer is in the form of a sheath applied about a portion of the cylindrical outer surface.

5. The tampon and delivery system of claim 4, wherein the sheath is comprised of a flexible sheet of delivery layer material wrapped about the cylindrical outer surface of the tampon and attached to itself.

6. The tampon and delivery system of claim 5, wherein the sheath is not directly adhered to the tampon.

7. The tampon and delivery system of claim 1, wherein the outer delivery layer is designed to break apart in the presence of fluid as the tampon radially swells due to absorbing fluid.

8. The tampon and delivery system of claim 1, wherein the outer delivery layer is formulated so as to adhere to vaginal wall.

9. The tampon and delivery system of claim 1, wherein the outer delivery layer is positioned at a distance of about 5 to 6 mm from the leading end of the tampon.

10. The tampon and delivery system of claim 1, wherein the outer delivery layer is formulated with about 1 to 100 mg of the pharmaceutical, holistic or medicinal component.

11. The tampon and delivery system of claim 1, wherein the delivery layer is about 1 mil to 4 mil in thickness.

12. A tampon and delivery system for a pharmaceutical, holistic or medicinal component, comprising:
   a tampon having a generally cylindrical shape including a leading end and a cylindrical outer surface;
   an outer delivery sheath applied to at least a portion of the cylindrical outer surface of the tampon and positioned at a distance from the leading end of the tampon so as to expose the leading end of the tampon, the outer delivery sheath including a first inner radial layer and a second outer radial layer, wherein at least one of the first or second radial layers is comprised of (a) a water soluble polymer film carrier formulated with (b) a pharmaceutical, holistic or medicinal component; and
   an applicator containing the tampon and the applied outer delivery sheath.

13. The tampon and delivery system of claim 12, wherein each of the first and second radial layers are comprised of (a) a water soluble polymer film carrier formulated with (b) a pharmaceutical, holistic or medicinal component, and the second outer radial layer is formulated to dissolve more quickly than the first inner radial layer.

14. The tampon and delivery system of claim 13, wherein the second outer radial layer comprises a larger dose of the pharmaceutical, holistic or medicinal component as compared to the first inner radial layer.

15. The tampon and delivery system of claim 12, wherein the second outer radial layer comprises a larger dose of the pharmaceutical, holistic or medicinal component as compared to the first inner radial layer.

16. The tampon and delivery system of claim 12, wherein the second outer radial layer is comprised of (a) a water soluble polymer film carrier formulated with (b) a pharmaceutical, holistic or medicinal component and the first inner radial layer is formulated so as to provide an absorption barrier between the tampon and the second outer radial layer.

17. A tampon and delivery system for a pharmaceutical, holistic or medicinal component, comprising:
   a tampon having a generally cylindrical shape including a leading end and a cylindrical outer surface;
   an outer delivery sheath applied to at least a portion of the cylindrical outer surface of the tampon, the outer delivery sheath including a first inner radial layer and a second outer radial layer;
   and an applicator containing the tampon and the applied outer delivery sheath;
   wherein each of the first and second radial layers are comprised of (a) a water soluble polymer film carrier and (b) a pharmaceutical, holistic or medicinal component and the pharmaceutical, holistic or medicinal component is different for each of the first and second radial layers.

18. The tampon and delivery system of claim 17, wherein the pharmaceutical, holistic or medicinal component of the second outer radial layer is formulated to have a more localized effect as compared to the first inner radial layer, and the pharmaceutical, holistic or medicinal component of the first inner radial layer is formulated to have a more systemic effect as compared to the second outer radial layer.

19. A method for constructing a tampon and delivery system for a pharmaceutical, holistic or medicinal component, comprising the steps of:
   providing a tampon having a generally cylindrical shape including a leading end and a cylindrical outer surface;
   applying an outer delivery sheath to at least a portion of the cylindrical outer surface of the tampon, positioning the outer delivery sheath at a distance from the leading end, the outer delivery sheath including (a) a water soluble polymer film carrier formulated with (b) a pharmaceutical, holistic or medicinal component; and
   installing the tampon and applied outer delivery sheath into an applicator.

20. The method of claim 19, wherein the applying step includes the following steps:
   providing a web of flexible material including (a) the water soluble polymer film carrier formulated with (b) the pharmaceutical, holistic or medicinal component;
   cutting a rectangular tab from the flexible web; and
   wrapping the rectangular tab about the cylindrical outer surface of the tampon.

21. The method of claim 20, wherein the applying step further comprises adhering opposing ends of the rectangular tab to each other after the wrapping step.

22. The method of claim 20, wherein the sheath includes two layers, at least one of the two layers including (a) the water soluble polymer film carrier formulated with (b) the pharmaceutical, holistic or medicinal component.

23. The method of claim 19, wherein the sheath includes two layers, at least one of the two layers including (a) the water soluble polymer film carrier formulated with (b) the pharmaceutical, holistic or medicinal component.

24. The method claim 19, wherein the applying step positions the sheath at a distance of about 5 to 6 mm from the leading end.

25. The method claim 19, wherein the sheath is about 1 mil to 4 mil in radial thickness.

\* \* \* \* \*